United States Patent
Thorsen et al.

(10) Patent No.: US 9,900,003 B2
(45) Date of Patent: Feb. 20, 2018

(54) HIGH VOLTAGE CURRENT SWITCH CIRCUIT

(71) Applicant: Fondazione Don Carlo Gnocchi Onlus, Milan (IT)

(72) Inventors: Rune Asbjoern Thorsen, Monza (IT); Luca Lombardini, Settimo Milanese (IT); Maurizio Ferrarin, Milan (IT)

(73) Assignee: Fondazione Don Carlo Gnocchi Onlus, Milan (IT)

( * ) Notice: Subject to any disclaimer, the term of this patent is extended or adjusted under 35 U.S.C. 154(b) by 21 days.

(21) Appl. No.: 14/380,203

(22) PCT Filed: Feb. 11, 2013

(86) PCT No.: PCT/EP2013/052672
§ 371 (c)(1),
(2) Date: Aug. 21, 2014

(87) PCT Pub. No.: WO2013/124178
PCT Pub. Date: Aug. 29, 2013

(65) Prior Publication Data
US 2015/0057539 A1 Feb. 26, 2015

(30) Foreign Application Priority Data

Feb. 22, 2012 (IT) .............................. TV2012A0026

(51) Int. Cl.
*H03K 17/687* (2006.01)
*H03K 17/722* (2006.01)
(Continued)

(52) U.S. Cl.
CPC ............. *H03K 17/687* (2013.01); *A61B 8/56* (2013.01); *A61N 1/36003* (2013.01);
(Continued)

(58) Field of Classification Search
CPC .. H03K 17/687; H03K 17/722; H03K 17/693; H03K 17/002; H03K 3/57; A61N 1/36125; A61N 1/36003; A61B 8/56
(Continued)

(56) References Cited

U.S. PATENT DOCUMENTS 5,033,468 A 7/1991 Takeuchi et al.
5,052,391 A 10/1991 Silberstone et al.
(Continued)

*Primary Examiner* — Lincoln Donovan
*Assistant Examiner* — Colleen O Toole
(74) *Attorney, Agent, or Firm* — Polsinelli PC

(57) ABSTRACT

The present invention relates to a high voltage switch circuit, comprising an input port adapted to receive a pulse type input current and an output port, which can be used selectively to conduct an output current to a corresponding electrical load. The switch circuit comprises a buffer stage adapted to sense the input voltage at said input port and to provide a buffered voltage that follows said input voltage. The switch circuit comprises complementary switches electrically connected between said input port and said output port and a voltage level translator electrically connected with said switches, said buffer stage and a control terminal that provides a control signal. The voltage level translator provides suitable gate voltages at the gate terminals of said switches, so that the operation of these latter can be controlled by said control signal.

12 Claims, 7 Drawing Sheets

(51) Int. Cl.
    *H03K 3/57*         (2006.01)
    *A61N 1/36*         (2006.01)
    *A61B 8/00*         (2006.01)

(52) U.S. Cl.
    CPC ..... *A61N 1/36014* (2013.01); *A61N 1/36125* (2013.01); *H03K 3/57* (2013.01); *H03K 17/722* (2013.01)

(58) Field of Classification Search
    USPC .......................... 341/141; 327/306, 320, 333
    See application file for complete search history.

(56) References Cited

U.S. PATENT DOCUMENTS

| | | | |
|---|---|---|---|
| 8,473,069 B2 * | 6/2013 | Bi ........................ | A61N 1/025 607/63 |
| 8,560,081 B2 * | 10/2013 | Cilingiroglu ........ | A61N 1/3787 607/11 |
| 2001/0051817 A1 * | 12/2001 | Sullivan .................. | A61N 1/39 607/5 |
| 2009/0132010 A1 | 5/2009 | Kronberg | |

* cited by examiner

HIGH VOLTAGE CURRENT SWITCH CIRCUIT

CROSS REFERENCE TO RELATED APPLICATIONS

This application is a National Phase filing under 35 U.S.C. § 371 of PCT/EP2013/052672 filed on Feb. 11, 2013; and this application claims priority to Application No. TV2012A000026 filed in Italy on Feb. 22, 2012; the entire contents of each application is hereby incorporated by reference.

The present invention relates to an electronic circuit of analog type, which can be of integrated type or realized with discrete components.

In particular, the present invention relates to a high voltage switch circuit for switching current signals, namely pulse type current signals, between an input port and a selectable output port.

In many applications, for example in the biomedical sector, multiplexers are used when it is necessary to supply a desired current signal to an output port, which can be activated selectively.

Italian patent application nr. MI2007A000595 describes a high voltage pulsed current generation circuit for a neuromuscular electrical stimulator. This document shows the use of a multiplexer having an input port adapted to receive a pulse type current signal, generated by a stimulation circuit, and a plurality of output ports, each of which can be selected to provide said current signal to a corresponding pair of stimulation electrodes.

Multiplexers, substantially of a type similar to the one described above, can also be used in biomedical applications of different type, such as in ultrasonic scanning apparatus.

Often, these devices do not have satisfactory galvanic isolation to ground of the output ports.

In many devices, even if intended for use, for example, in biomedical applications, in which the presence of effective galvanic isolation is a very important design requirement, it is possible to encounter the presence of non-negligible leakage currents to ground. The intensity of said leakage currents increases, generally not linearly, with the voltage at the terminals of the input/output port.

Many prior art multiplexers have high power consumption, both in stand-by mode and during operation, which increases significantly if high voltages are present at the terminals of the input/output ports.

Another example of electronic stimulation device is disclosed in U.S. Pat. No. 5,052,391.

In this document, an electronic circuit to provide high voltage, high rise-time, and charge balanced current pulses is disclosed.

This electronic circuit does not actually have current multiplexing functionalities but it basically provides for the splitting of one output for a parallel connection with a plurality of output channels.

Moreover, such a circuit shows relevant drawbacks in terms of weight and size, since multiple transformers have to be used to transfer the energy of a stimulation pulse to the corresponding output channels. The overall bulkness of such a system makes it difficult to use in portable stimulators.

Further, the output current supplied to each output port is often subject to relevant waveform distortions due to the currents adsorbed by the adopted switching devices.

The main object of the present invention is to provide a switch circuit, which is capable of overcoming the drawbacks described above.

A further object of the present invention is to provide a switch circuit that can be controlled by logic type signals to switch an input current towards a selectable output port.

A further object of the present invention is to provide a switch circuit, in which input and output terminals have high impedance to ground for voltages within the specification ranges.

A further object of the present invention is to provide a switch circuit having low quiescent and active power consumption for voltages within the specification ranges.

A further object of the present invention is to provide a switch circuit that can be supplied by high voltage power supplies.

A further object of the present invention is to provide a switch circuit that is easy to produce at industrial level, as an integrated circuit or as a discrete component circuit, at competitive costs with respect to prior art devices.

These objects, together with other objects that will be more apparent from the subsequent description and from the accompanying drawings, are achieved, according to the invention, by a high voltage switch circuit according to claim 1, proposed hereafter, and the related dependent claims which refer to preferred embodiments of the present invention.

Further characteristics and advantages of the present invention will be more apparent with reference to the description given below and to the accompanying figures, provided purely for explanatory and non-limiting purposes, wherein.

Figure 3:
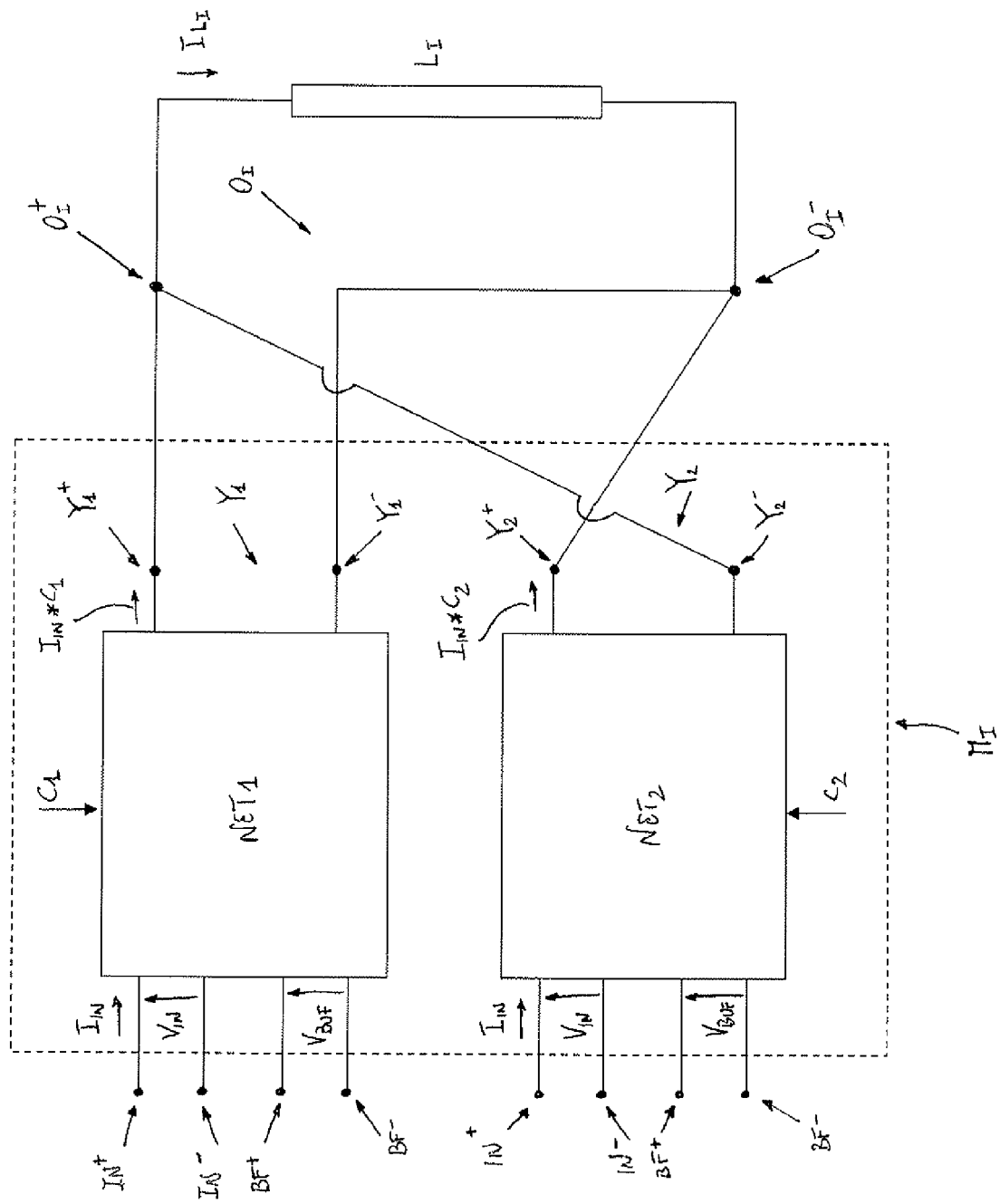
FIG. 3 illustrates a block diagram of the output stage included in an embodiment the high voltage switch circuit, according to the invention.
Figure 4:
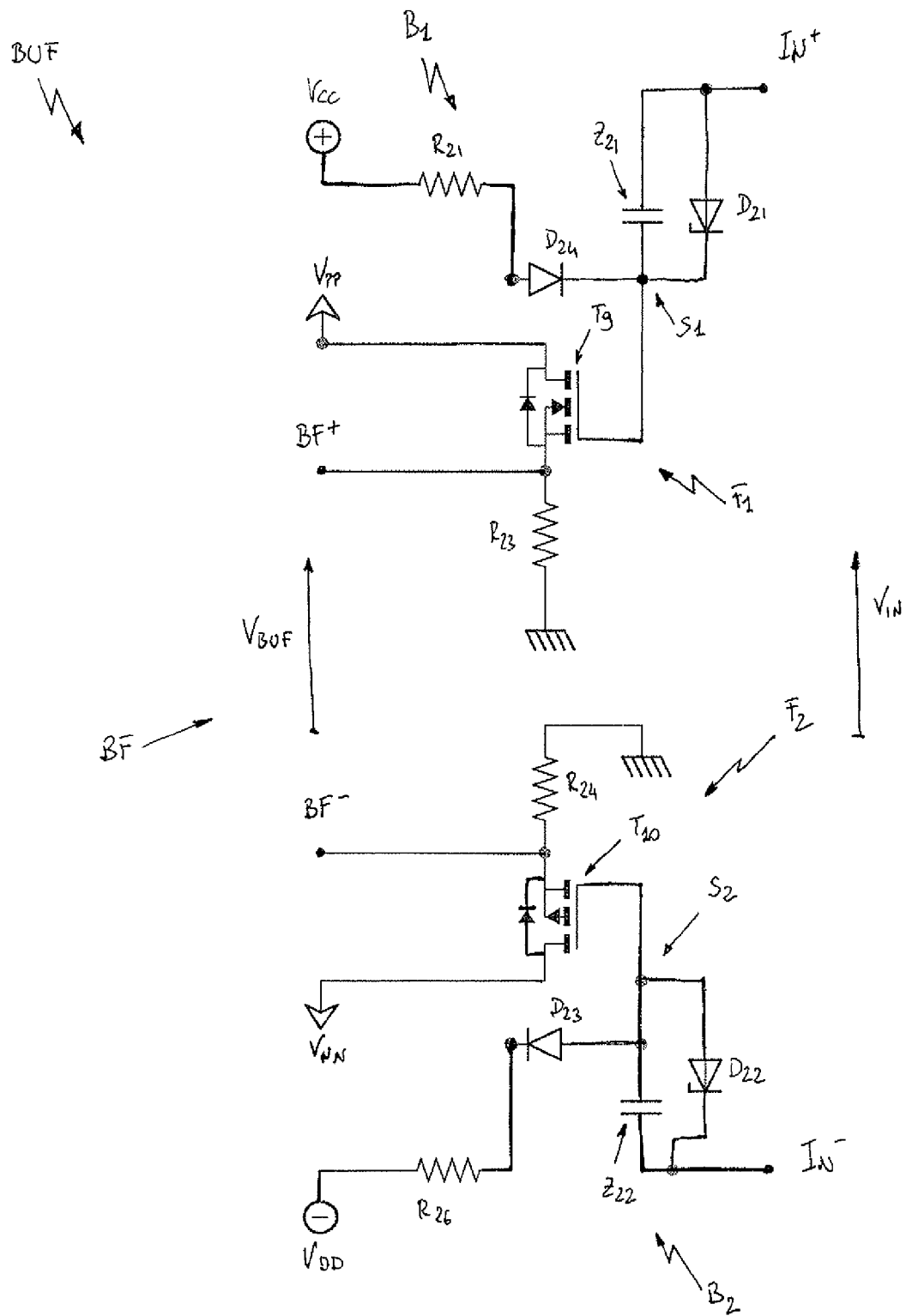
Figure 5:
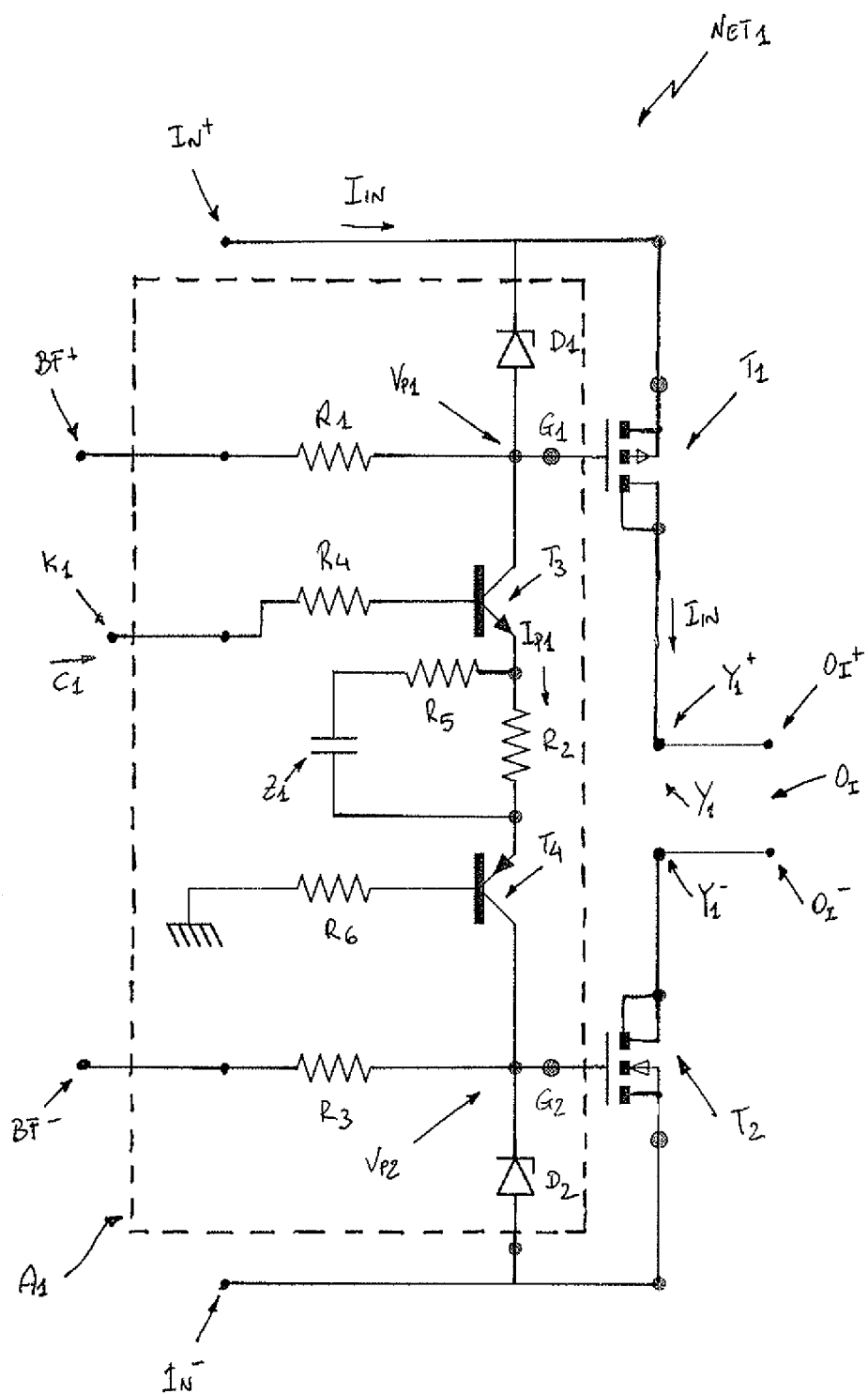
Figure 6:
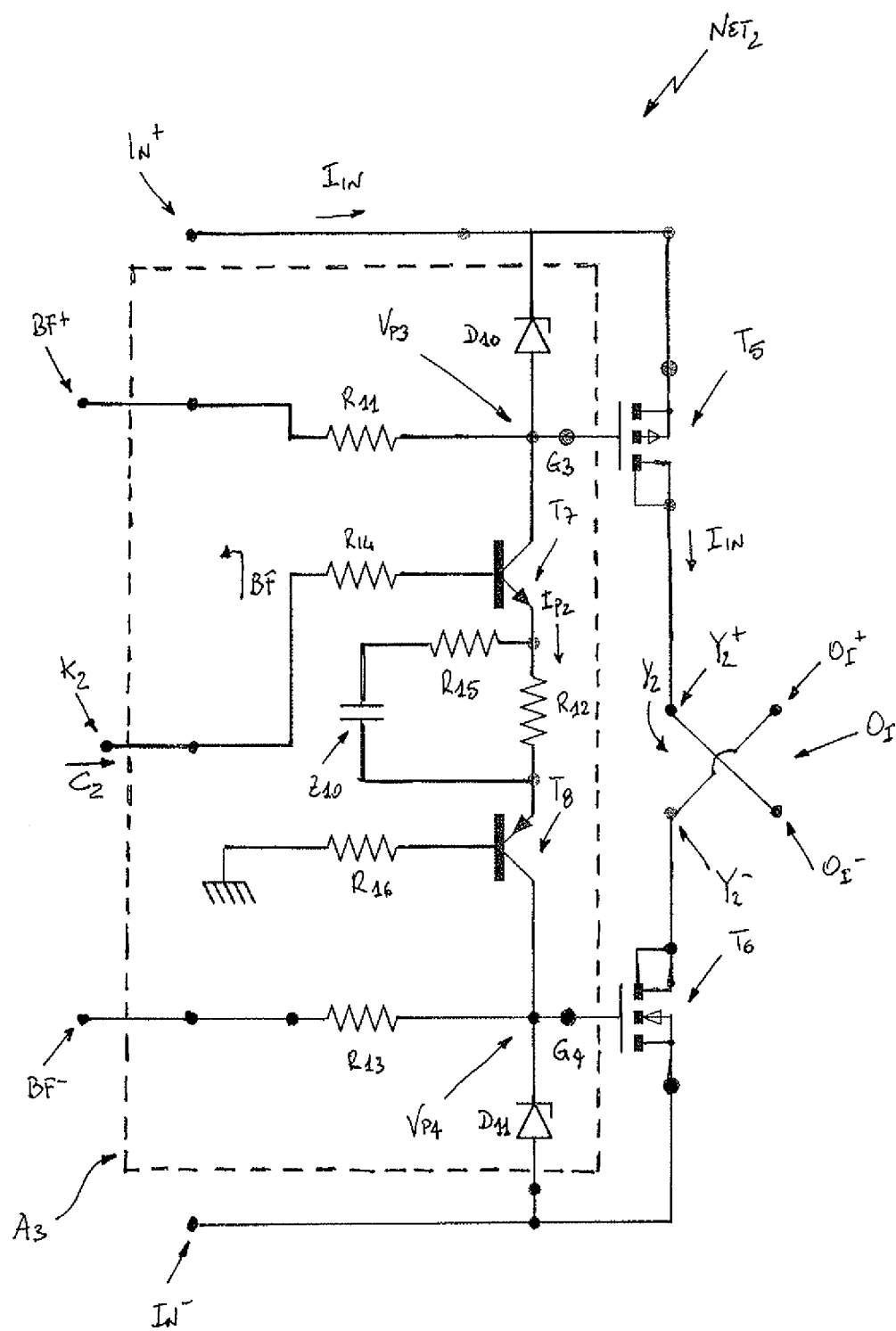

FIG. 4 schematically illustrates the buffer stage included in the high voltage switch circuit, according to the invention;

FIG. 5-6 illustrate in more details the circuit structure of the output stage of the high voltage switch circuit, in the embodiment shown in FIG. 3.

With reference to the aforesaid figures, the present invention relates to a high voltage switch circuit 1.

The high voltage switch circuit 1 is particularly adapted for use in a muscular or neuromuscular electrical stimulator and it will now be described with reference to such an implementation for simplicity of exposition.

However, this is not intended to limit in any way the scope of the present invention.

In fact, the switch circuit 1 can be used in different biomedical applications, for example in an ultrasonic devices, or in other types of devices in which it is necessary to selectively activate a plurality of current controlled ports, such as micro-electromechanical devices or systems (MEMS).

Figure 1A:
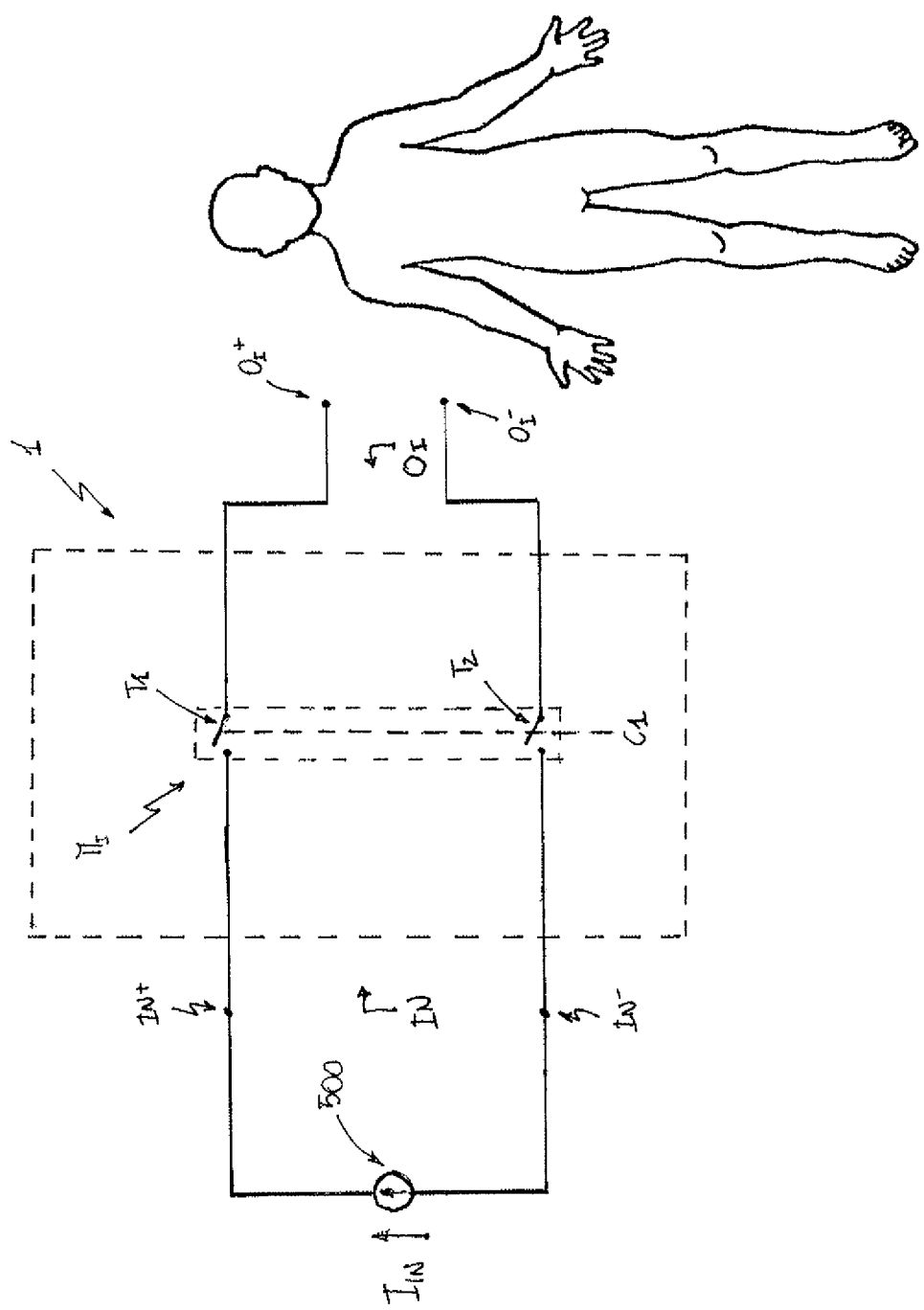
FIG. 1A, 1B illustrate block diagrams showing the general operation and structure of the high voltage switch circuit, according to the present invention.
Figure 1B:
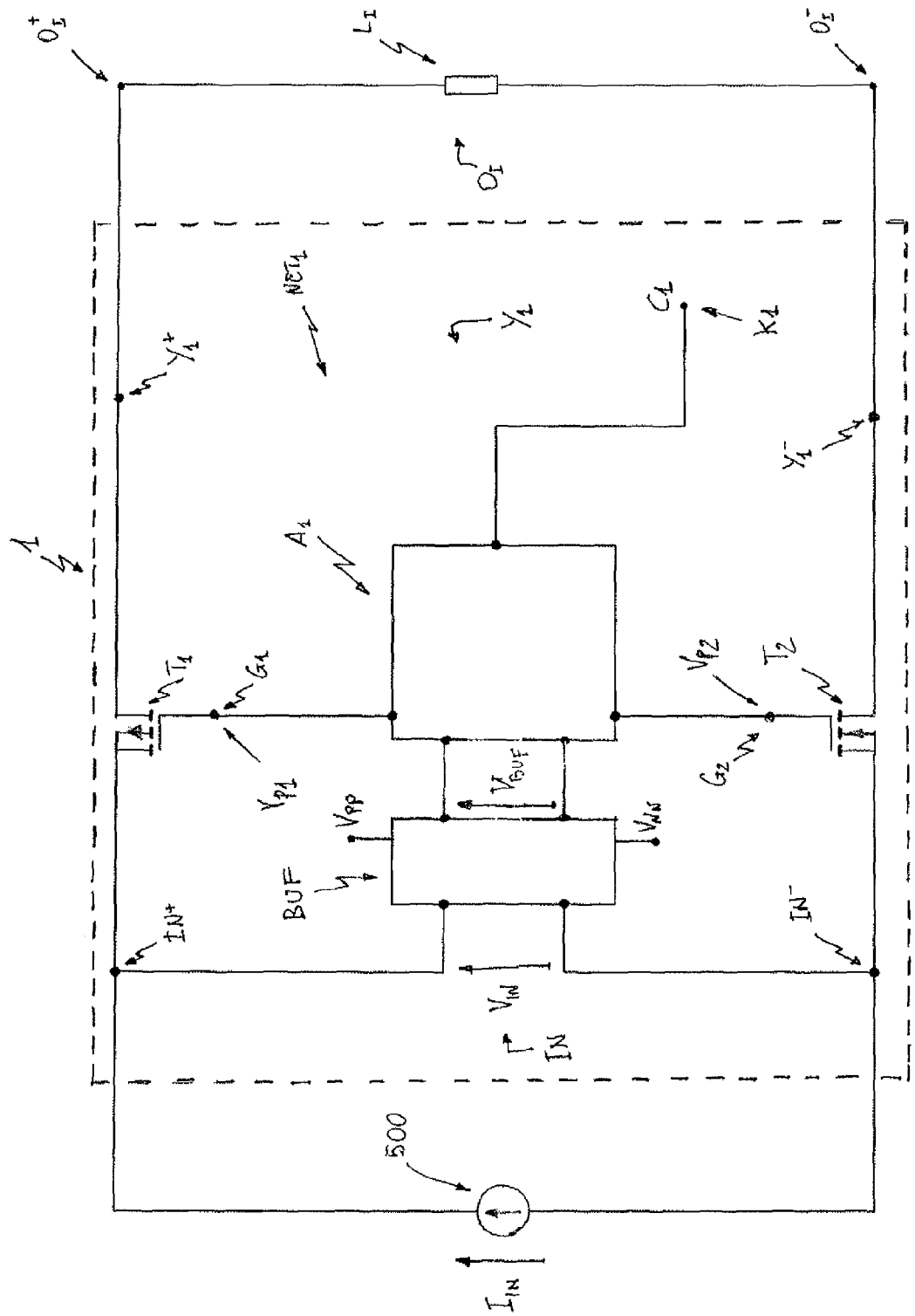

Referring to FIGS. 1A-1B, the switch circuit 1 comprises an input port IN adapted to receive an input current $I_{IN}$.

The input current $I_{IN}$ is predefined and is generated by a current generator circuit 500, electrically connected with a pair of terminals (positive and negative) IN⁺ and IN⁻ of the input port IN.

The input current $I_{IN}$ has a pulse type waveform, preferably of unipolar type.

The switch circuit 1 comprises an output port $O_I$ that can receive the input current $I_{IN}$ and conduct an output current $I_{LI}$ to a corresponding electrical load $L_I$.

The switch circuit 1 is capable of directing the input current $I_{IN}$ to the output port $O_I$, when this latter is selected to conduct the output current $I_{LI}$ to the load $L_I$.

An input voltage $V_{IN}$ is present between the terminals $IN^+$ and $IN^-$ of the input port IN, which is a function of the input current $I_{IN}$ and of the downstream equivalent impedance seen from the terminals of the input port IN.

The input voltage $V_{IN}$ can assume high values, for example values of a few hundreds of volts in an electrical stimulator.

The switch circuit 1 comprises an electronic buffer stage BUF that is electrically connected to the input port IN.

The buffer stage BUF is adapted to sense the input voltage $V_{IN}$, at the terminals $IN^+$, $IN^-$ of the input port IN, and to supply, at a buffer output BF, a buffered voltage $V_{BUF}$, which follows the sensed input voltage $V_{IN}$.

The switch circuit 1 comprises complementary switches $T_1$, $T_2$ that operate as current switches and are electrically connected between the input port IN and the output port $O_I$.

The switch circuit 1 comprises a first control terminal $K_1$ for providing a first control signal $C_1$ of logic type (for example at 0V and 3.3V).

Preferably, the switch circuit 1 is operatively associated with an electronic control stage COM adapted to generate the control signal $C_1$ and send it to the control terminal $K_1$, connected thereto.

In some embodiments of the present invention, the control stage COM may be physically included in the switch circuit 1.

Preferably, the control stage COM may comprise a digital processing device, for example a microprocessor, or a shift register or another circuit of similar type.

The switch circuit 1 comprises a first voltage level translator $A_1$ that is electrically connected with the buffer stage BUF, with the switches $T_1$, $T_2$ and with the control terminal $K_1$.

The voltage level translator $A_1$ is adapted to provide a first and second gate voltage $V_{P1}$, $V_{P2}$ respectively at a first and second gate terminal $G_1$, $G_2$ of the first and second switch $T_1$, $T_2$ to control said switches through the control signal $C_1$.

Depending on the control signal $C_1$, the switches $T_1$, $T_2$ enable or disable the flow of the input current $I_{IN}$ from the input port IN to the output port $O_I$, thus providing or blocking a current path from the input port IN to the output port $O_I$ for the input current $I_{IN}$.

The connectivity between the input port IN and each output port $O_1$ is determined by the control signal $C_1$ that selects the output port $O_1$ to receive the input current $I_{IN}$.

The output current provided by the switches $T_1$, $T_2$ is thus equal to $(I_{IN}*C_1)$ where $C_1$ is a logic signal having logic values equal to 0 or 1.

The adoption of the voltage level translator $A_1$ for providing the gate voltages $V_{P1}$, $V_{P2}$ is quite advantageous since it allows to properly set the voltage across the gate-source junctions of the switches $T_1$, $T_2$ in order to make it possible to control (in particular to turn on) said switches through the control signal $C_1$. The switches $T_1$, $T_2$ are in fact transistors in which the voltage across the gate-source junction may vary, since they have the source terminals electrically connected with the terminals of the input port IN.

As shown in FIGS. 1B and 3, the switches $T_1$, $T_2$, the voltage level translator $A_1$ and the input terminal $K_1$ form an output circuit $NET_1$ that is comprised in an electronic output stage $M_I$ of the switch circuit 1.

The output stage $M_I$ is electrically connected to the input port IN, the buffer stage BUF, the output port $O_I$ and preferably to the control stage COM.

According to a preferred embodiment of the present invention (FIG. 4), the buffer stage BUF comprises a circuit structure divided into two sections, substantially symmetrical with respect to ground.

Each of the aforesaid sections comprises a sensing circuit $B_1$, $B_2$ arranged in such a manner as to sense the voltage of a corresponding terminal $IN^+$, $IN^-$ of the input port IN, and a voltage follower circuit $F_1$, $F_2$, arranged in such a manner that the voltage of the positive and negative terminals $BF^+$, $BF^-$ of the buffer output BF follow the sensed voltage.

This solution makes it possible to maintain a high impedance to ground for the input port IN and the buffer output BF, the voltages at the terminals of which are floating with respect to ground.

The buffer output BF provides, between the terminals $BF^+$, $BF^-$, the buffered voltage $V_{BUF}$ that follows the variations of the voltage $V_{IN}$ at the terminals $IN^+$, $IN^-$ of the input port IN.

This makes it possible to power the voltage level translator $A_1$ with high voltages ($V_{PP}$ and $V_{NN}$) that are different from $V_{IN}$, thereby without introducing significant distortions (for example due to unwanted current absorptions) in the input current $I_{IN}$, when this latter flows toward the output port $O_I$.

In a first section, the buffer stage BUF preferably comprises a first sensing circuit $B_1$ and a first follower circuit $F_1$.

Preferably, the sensing circuit $B_1$ is electrically connected with the positive terminal $IN^+$ of the input port IN, with the sensing node $S_1$ and with a first power supply $V_{CC}$.

The sensing circuit $B_1$ senses the voltage of the positive terminal $IN^+$ of the input port IN and establishes an offset with respect to this voltage to compensate the threshold gate-source voltage of a transistor $T_9$ of the voltage follower circuit $F_1$ and prevent an unwanted conduction of the switch $T_1$.

Preferably, the sensing circuit $B_1$ comprises a Zener diode $D_{21}$ and a capacitor $Z_{21}$, connected in parallel between the positive terminal $IN^+$ and the sensing node $S_1$.

The diode $D_{21}$ advantageously prevents from over-voltages at the sensing node $S_1$ while the capacitor $Z_{21}$ maintains the voltage offset with respect to the voltage of the positive terminal $IN^+$.

Preferably, the sensing circuit $B_1$ comprises a resistor $R_{21}$ and a diode $D_{24}$ electrically connected in series between the power supply $V_{CC}$ and the sensing node $S_1$.

The voltage follower circuit $F_1$ is electrically connected with the sensing node $S_1$, with the positive terminal $BF^+$ of the buffer output BF and with a second power supply $V_{PP}$, which is a high voltage power supply.

In the voltage follower circuit $F_1$, the voltage of the positive terminal $BF^+$ substantially follows the voltage of the positive terminal $IN^+$.

Preferably, the voltage follower circuit $F_1$ comprises the transistor $T_9$, for example an n-type enhancement mode MOSFET, connected between the power supply $V_{PP}$ and ground through the resistor $R_{23}$.

The transistor $T_9$ has the gate terminal connected with the sensing node $S_1$, the drain terminal connected with the power supply $V_{PP}$ and the source terminal connected with the terminal $BF^+$ and to a resistor $R_{23}$, in turn connected with ground.

Operation of the first section of the stage BUF is now described in greater detail.

When there is no current flow towards the load $L_I$ (e.g. the input current $I_{IN}$ has no current pulses) the sensing node $S_1$ is at a voltage approximately equal to $V_{CC}$.

The voltage of the terminal $BF^+$ is therefore approximately equal to $V_{IN}$ minus the voltage drop on the network composed of the circuit elements $D_{21}$, $Z_{21}$, $D_{24}$ and $R_{21}$ and the voltage $V_{GSth}(T9)$, i.e. the threshold gate-source voltage of the transistor $T_9$.

The voltage of the sensing node $S_1$ follows the voltage of the terminal $IN^+$, so that the voltage of the terminal $BF^+$ follows the voltage of the terminal $IN^+$ and the switch $T_1$ is in an OFF state.

If there is a current flowing toward the load $L_I$ (i.e. the switch $T_1$ is in an ON state), the voltage of the terminal $IN^+$ depends substantially on the voltage drop across said load. In this case, the voltage variations at the terminal $IN^+$ are sensed by the sensing circuit $B_1$ and followed by the voltage at the terminal $BF^+$.

A second section of the buffer stage BUF preferably has a circuit structure substantially symmetrical to that of the first section described above, which comprises a second sensing circuit $B_2$ and a second follower circuit $F_2$.

Preferably, the sensing circuit $B_2$ is electrically connected with the negative terminal $IN^-$ of the input port IN, with a second sensing node $S_2$ and with a third power supply $V_{DD}$.

The sensing circuit $B_2$ senses the voltage of the negative terminal $IN^-$ of the input port IN and establishes a voltage offset with respect thereto to compensate the threshold gate-source voltage of a transistor $T_{10}$ of the voltage follower circuit $F_2$ and prevent an unwanted conduction of the switch $T_2$.

Preferably, the sensing circuit $B_2$ comprises a Zener diode $D_{22}$ and a capacitor $Z_{22}$, connected in parallel between the negative terminal $IN^-$ and the sensing node $S_2$.

The diode $D_{22}$ advantageously prevents from over-voltages at the sensing node $S_2$ while the capacitor $Z_{22}$ maintains the voltage offset with respect to the voltage of the negative terminal $IN^-$.

Preferably, the sensing circuit $B_2$ comprises a resistor $R_{26}$, and a diode $D_{23}$ electrically connected in series between the power supply $V_{DD}$ and the sensing node $S_2$.

The follower circuit $F_2$ is electrically connected with the sensing node $S_2$ and with the negative terminal $BF^-$ of the buffer output BF.

In the follower circuit $F_2$, the voltage of the negative terminal $BF^-$ substantially follows the voltage of the negative terminal $IN^-$.

Preferably, the follower circuit $F_2$ comprises the transistor $T_{10}$, for example a p-type enhancement mode MOSFET, connected between a fourth power supply $V_{NN}$, which is a high voltage power supply, and ground through the resistor $R_{24}$.

In the transistor $T_{10}$, the gate terminal is connected with the sensing node $S_2$, the drain terminal is connected with the power supply voltage $V_{NN}$ and the source terminal of the transistor $T_{10}$ is electrically connected with the terminal $BF^-$ and to a resistor $R_{24}$, in turn connected with ground.

Operation of the second section of the stage BUF is substantially similar to that of the first section.

When there is no current flow toward the load $L_I$ (e.g. the input current $I_{IN}$ does not have current pulses), the sensing node $S_2$ is at a voltage approximately equal to $V_{DD}$.

The voltage of the terminal $BF^-$ is therefore approximately equal to $V_{IN}$ minus the voltage drop on the network composed of the circuit elements $D_{22}$, $Z_{22}$, $D_{23}$ and $R_{26}$ and the voltage $V_{GSth}(T10)$, i.e. the threshold gate-source voltage of the transistor $T_{10}$.

The voltage of the sensing node $S_2$ follows the voltage of the terminal $IN^-$, so that the voltage of the terminal $BF^-$ follows the voltage of the terminal $IN^-$ and the switch $T_2$ is in OFF state.

If there is current flow toward the load $L_I$ (i.e. the switch $T_2$ is in ON state), the voltage of the terminal $IN^-$ depends substantially on the voltage drop across said load.

In this case, the voltage variations at the terminal $IN^-$ are sensed by the sensing circuit $B_2$ and followed by the voltage at the terminal $BF^-$.

The buffer stage BUF is thus capable to supply a buffered voltage $V_{BUF}$ that follows the input voltage $V_{IN}$ with a small power consumption and negligible distortions of the input current $I_{IN}$.

The structure of the first output circuit $NET_T$, in a preferred embodiment of the switch circuit 1 of the present invention (FIGS. 3 and 5), is now described in greater detail.

As mentioned above, the output circuit $NET_T$ comprises the switches $T_1$, $T_2$, the voltage level translator $A_1$ and the control terminal $K_1$.

Preferably, the output circuit $NET_T$ comprises a first output $Y_1$ electrically connected with the output port $O_I$.

The first output $Y_1$ comprises a pair of terminals (positive and negative) $Y_1^+$, $Y_1^-$ electrically connected with a pair of terminals (positive and negative) $O_I^+$, $O_I^-$ the output port $O_I$.

As shown in FIG. 3, the output $Y_1$ is electrically connected with the output port $O_I$ in such a manner that the output current $I_{LI}$, which is supplied by the output port $O_I$ to the corresponding electrical load $L_I$, has a waveform with the same polarity as the input current $I_{IN}$.

In this case, the terminals $Y_1^+$, $Y_1^-$ of the output $Y_1$ are electrically connected with the terminals $O_I^+$, $O_I^-$ the output port $O_I$ with direct polarity, i.e. with the positive terminal $Y_1^+$ electrically connected with the positive terminal $O_I^+$ and the negative terminal $Y_1^-$ electrically connected with the negative terminal $O_I^+$ the output port $O_I$.

Of course, the output $Y_1$ may be electrically connected with the output port $O_I$ in such a manner that the output current $I_{LI}$ has a waveform with reversed polarity with respect to the input current $I_{IN}$.

The switch $T_1$ is electrically connected between the positive terminal $IN^+$ of the input port $I_{IN}$ and the positive terminal $Y_1^+$ of the output $Y_1$ and the switch $T_2$ is electrically connected between the negative terminal $IN^-$ of the input port $I_{IN}$ and the negative terminal $Y_1^-$ of the output $Y_1$.

The switches $T_1$ and $T_2$ are complementary and are preferably field effect transistors (J-FETs or MOSFET), respectively of p- and n-enhancement mode type.

Advantageously, the transistors $T_1$ and $T_2$ are arranged to have the drain terminals electrically connected with the terminals $Y_1^+$ and $Y_1^-$ and the source terminals electrically connected with the terminals $IN^+$ and $IN^-$, respectively.

In this way, when the transistors $T_1$ and $T_2$ are in conduction state (switches $T_1$ and $T_2$ in ON state), the input current $I_{IN}$ can flow from the terminals of the input port IN to the terminals of the output $Y_1$.

Instead, when the two transistors $T_1$ and $T_2$ are in cut-off state (switches $T_1$ and $T_2$ in OFF state), the passing of the input current $I_{IN}$ toward the output $Y_1$ is prevented.

As mentioned above, the voltage level translator $A_1$ is advantageously adapted to control the switches $T_1$ and $T_2$ through the control signal $C_1$.

The voltage level translator $A_1$ is electrically connected between the terminals (positive and negative) $BF^+$, $BF^-$ of the buffer output BF and with the gate terminals $G_1$, $G_2$ of the switches $T_1$ and $T_2$.

The voltage level translator $A_1$ comprises a first polarization circuit including the circuit series of the resistor $R_1$, the third transistor $T_3$, the resistor $R_2$, the fourth transistor $T_4$ and the resistor $R_3$.

The transistors $T_3$, $T_4$ are preferably bipolar junction transistors (BJT), respectively of npn and pnp type, and are adapted to enable/prevent flow of a first polarization current $I_{P1}$ along said first polarization circuit.

The transistors $T_3$, $T_4$ are arranged in such a manner to be controlled by the terminal $K_1$, according to the state of the control signal $C_1$.

Preferably, the transistor $T_3$ has its collector terminal electrically connected with the resistor $R_1$, which is in turn connected in series with the positive terminal $BF^+$ of the buffer output BF, and is connected with the control terminal $K_1$, at the base terminal thereof.

Instead, the transistor $T_4$ has the base terminal connected to ground and the collector terminal electrically connected with the resistor $R_3$, which is in turn connected in series with the negative terminal $BF^-$ of the buffer output BF.

The transistors $T_3$ and $T_4$ have their emitter terminals connected with the terminals of the resistor $R_2$.

As an alternative, the transistors $T_3$, $T_4$ may have their base terminals connected to the ground and to the terminal $K_1$, respectively.

Preferably, the voltage level translator $A_1$ comprises a first circuit network to protect the switches $T_1$ and $T_2$ (in particular their gate terminals $G_1$, $G_2$) against over-voltages.

This protective network advantageously comprises first and second over-voltage protection elements $D_1$ and $D_2$ (preferably Zener diodes) that are respectively connected between the gate terminals $G_1$, $G_2$ of the transistors $T_1$ and $T_2$ and the terminals $IN^+$ and $IN^-$ of the input port IN.

Preferably, the voltage level translator $A_1$ also comprises some stabilizing circuit elements, such as the resistor $R_5$ and the capacitor $Z_1$, connected in parallel with the resistor $R_2$, and the protection resistor $R_4$ and $R_6$, connected in series with the base terminals of the transistor $T_3$ and $T_4$, respectively.

Operation of the output circuit $NET_1$ is now described in greater detail.

Let us assume that the output circuit $NET_1$ is initially in a deactivated or stand-by state and the terminal $K_1$ receives a control signal $C_1$ at "low" logic level.

The transistors $T_3$ and $T_4$ are in the cut-off state and there is no flow of the polarization current $I_{P1}$.

If the input current $I_{IN}$ does not have any current pulses, the voltage at the terminal $BF^+$ is approximately $V_{CC}-V_{GS}(T_9)$ while the voltage at the terminal $BF^-$ is approximately $V_{DD}-V_{GS}(T_{10})$, where $V_{GS}(T_9)$ and $V_{GS}(T_{10})$ are the gate-source voltages of the transistors $T_9$ and $T_{10}$, respectively.

If the input current $I_{IN}$ has a current pulse, the voltage at the terminals $BF^+$ and $BF^-$ increases up to $V_{PP}$ and $V_{NN}$ respectively.

In both cases, as there is no flow of the polarization current $I_{P1}$, the voltage level translator $A_1$ provides gate voltages $V_{P1}$, $V_{P2}$ to the gate terminals $G_1$, $G_2$, such as to maintain the switches $T_1$ and $T_2$ in the cut-off state.

From the above, it is evident how, with a control signal $C_1$ at a "low" logic level, whatever the voltage $V_{IN}$ and the input current $I_{IN}$ (within the specification range of the circuit), the switches $T_1$ and $T_2$ remain in the OFF state and the input current $I_{IN}$ cannot flow toward the output $Y_1$.

The output circuit $NET_1$ is therefore maintained in deactivated or stand-by state.

When the terminal $K_1$ receives a control signal $C_1$ at "high" logic level, the transistors $T_3$ and $T_4$ are taken to conduction state and the polarization current $I_{P1}$ can flow.

In this situation, before the switching of the transistors $T_3$, $T_4$ is completed, the voltage at the terminals $BF^+$ and $BF^-$ initially tends to increase up to $V_{PP}$ and $V_{NN}$ respectively.

Due to the voltage drop across the resistors $R_1$ and $R_3$, which is determined by flow of the current $I_{P1}$, the voltage level translator $A_1$ provides gate voltages $V_{P1}$, $V_{P2}$ to the gate terminals $G_1$, $G_2$, such as to take the switches $T_1$ and $T_2$ to the conduction state (ON state).

The switches $T_1$ and $T_2$ are taken to the ON state and the input current $I_{IN}$ is free to flow toward the output $Y_1$.

At this point, the voltage at the terminals $BF^+$ and $BF^-$ depends substantially on the voltage across the load $L_I$ but the voltage drop across the resistors $R_1$ and $R_3$, due to flow of the current $I_{P1}$, ensures that the gate terminals $G_1$, $G_2$ are always at voltages such as to maintain the switches $T_1$ and $T_2$ in conduction state.

Therefore, with a control signal $C_1$ at a high logic level, whatever the voltage $V_{IN}$ and the input current $I_{IN}$ (within the specification range of the circuit), the switches $T_1$ and $T_2$ are always in ON state and the input current $I_{IN}$ can flow toward the output $Y_1$.

From the above, it is apparent that the voltage level translator $A_1$ provides a voltage level shifting of the control signal $C_1$ to safely control the switches $T_1$, $T_2$, despite of the variations of the input voltage $V_{IN}$, since these latter are constantly followed by the buffered voltage $V_{BUF}$.

Given that the terminals of the output $Y_1$ are preferably connected with direct polarity to the terminals of the output port $O_I$, the output current $I_{IL}$ supplied to the electrical load $L_I$, has a waveform with the same polarity as the input current $I_{IN}$.

In other words, the condition $IL_I=I_{IN}$ is obtained.

In this way, when the output circuit $NET_1$ is enabled by the control signal $C_1$ to transmit an input current $I_{IN}$ of pulse type toward the output port $O_I$, the output current $I_{IL}$ has pulses with the same polarity and amplitude as the pulses of the input current $I_{IN}$.

When the terminal $K_1$ again receives a control signal $C_1$ at "low" logic level, the transistors $T_3$ and $T_4$ return to the cutoff state and ideally there should be no flow of the polarization current $I_{P1}$.

In this situation, in fact, the voltage level translator $A_1$ supplies, respectively to the gate terminals $G_1$, $G_2$ voltages $V_{P1}$, $V_{P2}$ such as to take the transistors $T_1$ and $T_2$ to cut-off state (OFF state).

Regardless of this, due to the presence of stray capacitances between the gate terminals $G_1$, $G_2$ and the terminal $IN^+$ of the input port IN, the transistors $T_1$, $T_2$ do not switch immediately but are taken to OFF state only when the input current $I_{IN}$ reaches zero, i.e. at the end of the input current pulse.

Based on the above, it can be observed that:
activation of the output circuit $NET_1$ is determined simply by the transition of the control signal $C_1$ from a "low" logic level to a "high" logic level;
deactivation of the output circuit $NET_1$ is instead determined by transition of the control signal $C_1$ to "low" logic level and by passage of the input current $I_{IN}$ through zero.

It is therefore evident how the output circuit $NET_1$ behaves, from a functional viewpoint, in a manner substantially similar to that of a DIAC electronic device.

In an embodiment of the present invention, particularly suitable for use in a muscular or neuromuscular electrical stimulator, the switch circuit 1 comprises the fifth and sixth complementary switches $T_5$, $T_6$ that operate as current switches and that are electrically connected between the input port IN and the output port $O_I$, in parallel with the switches $T_1$, $T_2$.

The switch circuit 1 comprises a second control terminal $K_2$ for providing a second control signal $C_2$ of logic type.

Preferably, the second control signal $C_2$ is received from the control stage COM.

The switch circuit 1 comprises a second voltage level translator $A_3$ that is electrically connected with the buffer stage BUF, with the switches $T_5$, $T_6$ and with the control terminal $K_2$.

The voltage level translator $A_2$ is adapted to provide a third and fourth gate voltage $V_{P3}$, $V_{P4}$ respectively at a third and fourth gate terminal $G_3$, $G_4$ of the switches $T_5$, $T_6$ in order to control these latter through the control signal $C_2$.

Depending on the control signal $C_2$, the switches $T_5$, $T_6$ can enable or disable the flow of the input current $I_{IN}$ from the input port IN to the output port $O_I$, thereby providing or blocking a current path from the input port $I_{IN}$ towards the output port $O_I$ for the input current $I_{IN}$.

The connectivity between the input port IN and each output port $O_I$ is determined by the control signal $C_2$ and the output current provided by the switches $T_5$, $T_6$ is thus equal to ($I_{IN}*C_2$), where $C_2$ is a logic signal having logic values equal to 0 or 1.

The adoption of the voltage level translator $A_3$ for providing the gate voltages $V_{P3}$, $V_{P4}$ is quite advantageous since it allows to properly set the voltage across the gate-source junction of the switches $T_5$, $T_6$ in order to make it possible to control (in particular to turn on) them through the control signal $C_2$.

As shown in FIGS. 3 and 6, the switches $T_5$, $T_6$, the voltage level translator $A_3$ and the control terminal $K_2$ form an output circuit $NET_2$, which is comprised in an output stage $M_I$ of the switch circuit 1 and which is connected between the input port IN and the output port $O_I$, as the output circuit $NET_1$.

Referring to FIG. 6, the output circuit $NET_2$ has a circuit structure similar to that of the circuit $NET_1$, described above.

The output circuit $NET_2$ comprises a second output $Y_2$ electrically connected with the output port $O_I$.

The second output $Y_2$ comprises a pair of terminals (positive and negative) $Y_2^+$, $Y_2^-$ electrically connected with the terminals $O_I^+$, $O_I^-$ the output port $O_I$.

Preferably, the output circuit $NET_2$ is electrically connected with the output port $O_I$ in such a manner that the output current $I_{LI}$, which is supplied by the output port $O_I$ to the corresponding electrical load $L_I$, has a waveform with reverse polarity with respect to that of the input current $I_{IN}$.

In this case, the terminals $Y_2^+$, $Y_2^-$ of the output $Y_2$ are electrically connected with the terminals $O_I^+$, $O_I^-$ the output port $O_I$ with reverse polarity, i.e. with the positive terminal $Y_2^+$ electrically connected with the negative terminal $O_I^-$ and the negative terminal $Y_2^-$ electrically connected with the positive terminal $O_I^+$ of the output port $O_I$.

Of course, the output circuit $NET_2$ may be electrically connected with the output port $O_I$ in such a manner that the output current $I_{LI}$ has a waveform with direct polarity with respect to the input current $I_{IN}$.

The switch $T_5$ is electrically connected between the positive terminal $IN^+$ of the input port $I_{IN}$ and the positive terminal $Y_2^+$ of the output $Y_2$ and the switch $T_6$ is electrically connected between the negative terminal $IN^-$ of the input port $I_{IN}$ and the negative terminal $Y_2^-$ of the output $Y_2$.

The switches $T_5$ and $T_6$ are complementary and preferably field effect transistors (FET or MOSFET), respectively of p- and n-port enhancement mode type.

Advantageously, the switches $T_5$ and $T_6$ are arranged in such a manner as to have the drain terminals electrically connected with the terminals $Y_2^+$ and $Y_2^-$ and the source terminals electrically connected with the terminals $IN^+$ and $IN^-$, respectively.

In this way, when the transistors $T_5$ and $T_6$ are in conduction state (switches $T_5$ and $T_6$ in ON state), the input current $I_{IN}$ can flow from the terminals of the input port IN to the terminals of the output $Y_2$.

Instead, when the transistors $T_5$ and $T_6$ are in the cut-off state (switches $T_5$ and $T_6$ in OFF state), the passage of the input current $I_{IN}$ toward the output $Y_2$ is prevented.

Preferably, the voltage level translator $A_3$, adapted to control the transistors $T_5$ and $T_6$, is electrically connected between the terminals (positive and negative) $BF^+$ and $BF^-$ of the buffer output BF and with the gate terminals $G_3$, $G_4$ of the switches $T_5$ and $T_6$.

The voltage level translator $A_3$ advantageously comprises a second polarization circuit formed by the circuit series consisting of the resistor $R_{11}$, the seventh transistor $T_7$, the resistor $R_{12}$, the eighth transistor $T_8$ and the resistor $R_{13}$.

The transistors $T_7$ and $T_8$ are preferably bipolar junction transistors (BJT), respectively of npn and pnp type, and are adapted to enable/prevent flow of a second polarization current $I_{P2}$ along said second polarization circuit.

Preferably, the transistor $T_7$ has its collector terminal electrically connected with the resistor $R_{11}$, in turn connected in series with the positive terminal $BF^+$ of the buffer output BF, and is connected with the terminal $K_2$, at the base terminal thereof.

The transistor $T_8$ has the base terminal connected with ground and the collector terminal electrically connected with the resistor $R_{13}$, in turn connected in series with the negative terminal $BF^-$ of the buffer output BF.

The transistors $T_7$ and $T_8$ have their emitter terminals connected to the terminals of the resistor $R_{12}$.

As an alternative, the transistors $T_7$, $T_8$ may have their base terminals connected to the ground and to the terminal $K_2$, respectively.

Preferably, the voltage level translator $A_3$ comprises a second circuit network to protect the gate terminals of the transistors $T_5$ and $T_6$ against over-voltages.

This protective network advantageously comprises third and fourth over-voltage protection elements $D_{10}$ and $D_{11}$ (preferably Zener diodes) that are respectively connected between the gate terminals $G_3$, $G_4$ of the transistors $T_5$ and $T_6$ and the terminals $IN^+$ and $IN^-$ of the input port IN.

Preferably, the voltage level translator $A_3$ also comprises some stabilizing circuit elements, such as the resistor $R_{15}$ and the capacitor $Z_{10}$, connected in parallel with the resistor $R_{12}$, and the protection resistor $R_{14}$ and $R_{16}$ connected in series with the base terminals of the transistors $T_7$ and $T_8$, respectively.

Operation of the output circuit $NET_2$ is similar to that of the output circuit $NET_1$.

Let us assume that the output circuit $NET_2$ is initially in a deactivated state and the terminal $K_2$ receives a logic control signal $C_2$ at "low" level. The transistors $T_7$ and $T_8$ are in the cut-off state and there is no flow of the polarization current $I_{P2}$.

In this situation, in the presence or absence of pulses of the input current $I_{IN}$, the gate terminals of the switches $T_5$ and $T_6$ are always at gate voltages $V_{P3}$, $V_{P4}$ such as to maintain them in a cut-off state.

Therefore, with a control signal $C_2$, at a low logic level, the switches $T_5$ and $T_6$ remain in the OFF state and the input current $I_{IN}$ cannot in any case flow toward the output $Y_2$.

The output circuit $NET_2$ is therefore maintained in a deactivated or stand-by state.

When the terminal $K_2$ receives a logic control signal $C_2$ at "high" level, the transistors $T_7$ and $T_8$ switch to conduction state and the polarization current $I_{P2}$ can flow.

In this situation, due to the voltage drop across the resistors $R_{11}$ and $R_{13}$, determined by the flow of the current $I_{P2}$, the gate terminals $G_3$, $G_4$ of the transistors $T_5$ and $T_6$ are polarized at gate voltages $V_{P3}$, $V_{P4}$ such as to take the transistors $T_5$ and $T_6$ to conduction state.

The switches $T_5$ and $T_6$ are then taken to the ON state and the input current $I_{IN}$ is free to flow toward the output $Y_2$.

At this point, the voltage at the terminals $BF^+$ and $BF^-$ depends substantially on the voltage across the load $L_I$ but the voltage drop across the resistors $R_{11}$ and $R_{13}$, due to circulation of the current $I_{P2}$, ensures that the gate terminals $G_3$, $G_4$ are always at gate voltages $V_{P3}$, $V_{P4}$ such as to maintain the transistors $T_5$ and $T_6$ in conduction state.

Therefore, with a control signal $C_2$ at high logic level, whatever the voltage $V_{IN}$ and the input current $I_{IN}$ (within the specification range of the circuit), the switches $T_5$ and $T_6$ are always in the ON state and the input current $I_{IN}$ can in any case flow toward the output $Y_2$.

From the above, it is apparent that the voltage level translator $A_3$ provides a voltage level shifting of the control signal $C_3$ to safely control the switches $T_5$, $T_6$, despite of the variations of the input voltage $V_{IN}$, since these latter are constantly followed by the buffered voltage $V_{BUF}$.

Given that the terminals of the output $Y_2$ are preferably connected with reverse polarity to the terminals of the output port $O_I$, the output current $I_{IL}$ supplied to the electrical load $L_I$, will have a waveform with reverse polarity with respect to the input current $I_{IN}$.

In other words, the condition $IL_I = -I_{IN}$ is obtained.

In this way, when the output circuit $NET_2$ is enabled by the control signal $C_2$ to transmit a pulse type input current $I_{IN}$ toward the output port $O_I$, the output current $I_{IL}$ has pulses with the same amplitude but with reverse polarity with respect to the pulses of the input current $I_{IN}$.

When the terminal $K_2$ once again receives a control signal $C_2$ at "low" logic level, the transistors $T_7$ and $T_8$ are again taken to the cutoff state and ideally there should be no flow of the polarization current $I_{P2}$.

In this situation, the voltage level translator $A_3$ supplies, respectively to the gate terminals of the transistors $T_5$ and $T_6$, gate voltages $V_{P3}$, $V_{P4}$ such as to take the same transistors $T_5$ and $T_6$ to the cut-off state.

Regardless of this, due to the presence of stray capacitances between the gate terminals of the transistors $T_5$, $T_6$ and the terminal $IN^-$ of the input port, the transistors $T_5$, $T_6$ do not switch immediately but are taken to the cut-off state only when the input current $I_{IN}$ reaches zero, i.e. at the end of the input current pulse.

On the basis of the above, it can be observed that:
activation of the output circuit $NET_2$ is determined simply by transition of the control signal $C_2$ from a "low" logic level to a "high" logic level;
deactivation of the output circuit $NET_2$ is determined by transition of the control signal $C_2$ at "low" logic level and by passage of the input current $I_{IN}$ through zero.

Therefore, also the output circuit $NET_2$ behaves, from a functional viewpoint, in a manner substantially similar to that of a DIAC electronic device.

Figure 2:
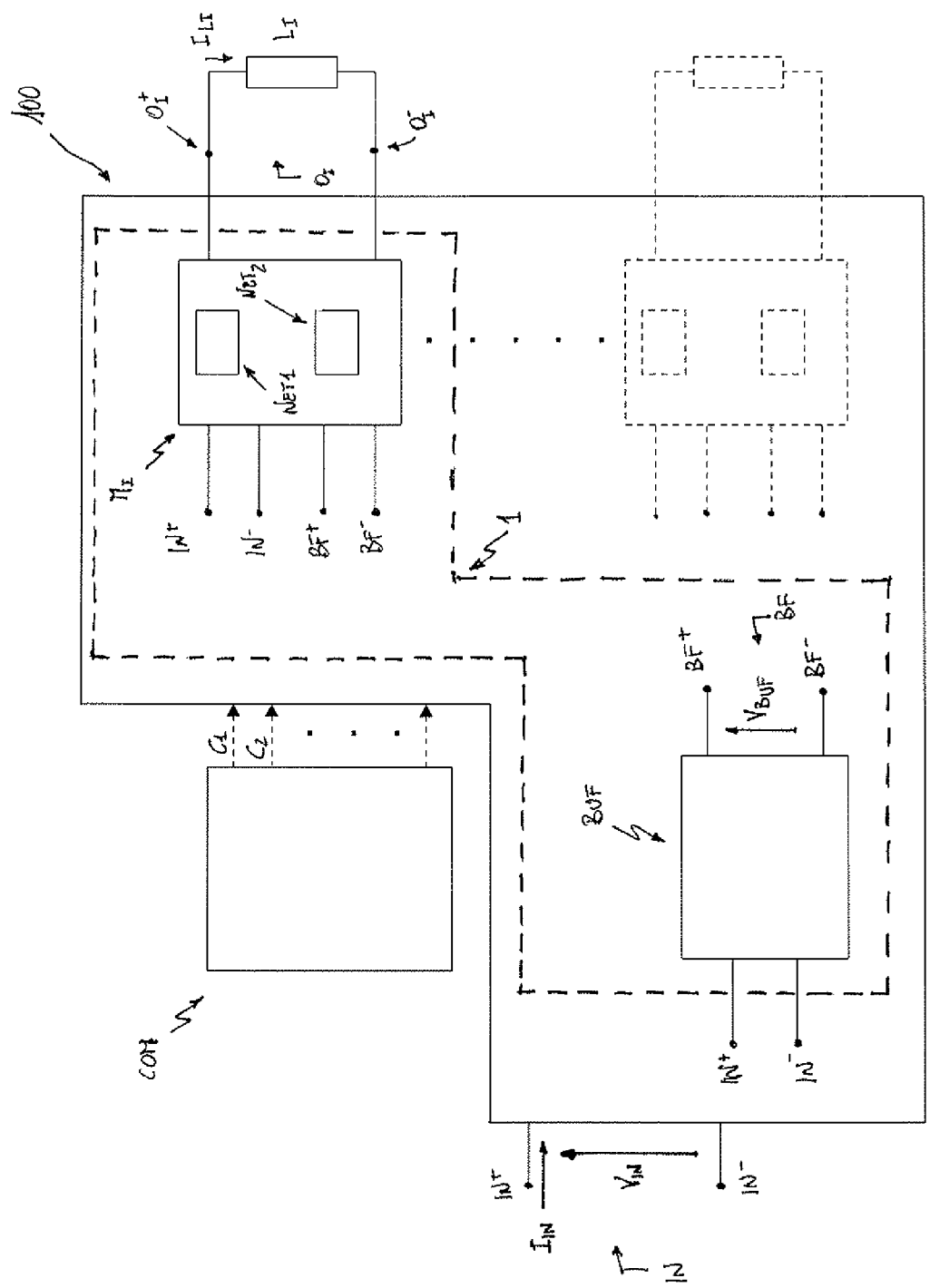
FIG. 2 illustrates a block diagram of a multiplexer comprising the high voltage switch circuit, according to the present invention.

Referring to FIG. 2, the high voltage switch circuit 1, which does not have multiplexing functionalities per se, is particularly suitable for implementation in a multiplexer 100.

The multiplexer 100 comprises a common input port IN and a plurality of output ports $O_I$, each of which can be selected by logic control signals.

The multiplexer 100 receives an input current $I_{IN}$ at the input port IN and it directs it towards the selected output ports $O_I$.

The multiplexer 100 thus implements a multiplexing function of the type 1→N, with N>1, for the current signals received at the input port IN.

The adoption of the high voltage switch circuit 1 in a multiplexer 100 is particularly advantageous for use in an electrical stimulator.

In this case, each of the mentioned output ports can be electrically connected with a pair of stimulation electrodes and the output current, supplied by each output port, is the current effectively injected by the electrodes during stimulation, while the electrical load connected to each output port typically consists of the impedance offered by the stimulation electrodes and by the portion of the patient's body affected by the stimulation current.

The multiplexer 100 comprises a common buffer stage BUF (as described above), which senses the voltage $V_{IN}$ between the terminals of the input port IN and provides, at the buffer output BF, a buffered voltage $V_{BUF}$ that substantially follows the input voltage $V_{IN}$.

The multiplexer 100 comprises a plurality of output stages $M_I$, each of which is electrically connected with the input port IN, the common buffer stage BUF and a corresponding output port $O_I$.

Each of the output stages $M_I$ comprises the output circuit $NET_1$ and preferably also the output circuit $NET_2$, as described above.

Preferably, the control terminals $K_1$ (and possibly $K_2$) of each output stage $M_I$ are electrically connected with a common control stage COM that may be physically included in the multiplexer 1.

It is apparent that the common buffer stage BUF and each of the output stages $M_I$ form a switch circuit 1, according to the invention, which is electrically connected between the input port IN and the corresponding output port $O_I$ (FIG. 2).

The operation of the multiplexer 100 is now briefly described.

Normally, the output stages $M_I$ are maintained in a deactivated state.

Therefore, the control signals sent by the control stage COM are normally maintained at a "low" logic level.

To direct the input current $I_{IN}$ toward any desired output port $O_I$, the control stage COM must activate the output circuit $NET_1$ (or optionally the output circuit $NET_2$) of the output stage $M_I$, which is operatively associated with the chosen output port $O_I$.

The control signal $C_1$ (or possibly $C_2$) sent to the output circuit $NET_1$ (or possibly $NET_2$) of the output stage $M_I$, is therefore taken to "high" logic level, enabling the input current $I_{IN}$ to flow toward the output port $O_I$.

If the output $Y_1$ (or possibly $Y_2$) of the output circuit $NET_1$ (or $NET_2$) is connected with direct polarity to the output port $O_I$, the output current $I_{IL}$ has the same waveform as the input current $I_{IN}$.

If the output $Y_1$ (or possibly $Y_2$) of the output circuit $NET_1$ (or $NET_2$) is connected with reverse polarity to the output port $O_I$, the output current $I_{IL}$ has a waveform with pulses of opposite polarity with respect to the input current $I_{IN}$.

It can be noted how by suitably managing the output circuit $NET_1$ (or NET), one or more pulses of the input current $I_{IN}$ can be "neutralized", simply by maintaining the control signals $C_1$ (or $C_2$) in the "low" logic state. The pulses of the input current $I_{IN}$ thus "neutralized", do not appear, with direct or reverse polarity, in the output current $I_{IL}$.

In this case, the output current $I_{IL}$ has a different time distribution of the pulses, with respect to the input current $I_{IN}$.

Operation of the output stage $M_I$, as adjusted by the control signals $C_1$, $C_2$, can be summarized in the following exemplificative table:

| $C_1$ | $C_2$ | $M_I$ | $I_{LI}$ |
|---|---|---|---|
| 0 | 0 | OFF | 0 |
| 0 | 1 | Circuit $NET_2$ ON (reversing) | $-I_{IN}$ |
| 1 | 0 | Circuit $NET_1$ ON (not reversing) | $I_{IN}$ |
| 1 | 1 | Short circuit | 0 ($V_{IN-o}$) |

From the table above it is evident how the output current from each output stage $M_I$ is equal to $(I_{IN}*C_1)$ or $(I_{IN}*C_2)$, where $C_1$, $C_2$ are logic signals that assume the logic values 0 or 1.

The multiplexer 1 is therefore not only capable of reversing the polarity of the pulses of the input current $I_{IN}$ (for example, by alternately activating the switching circuits $NET_1$ and $NET_{25}$ where both are present) but also of modifying the waveform of this latter.

The use of the switching circuits $NET_1$ and (optionally) $NET_2$ in each output stage $M_I$, with the functionalities described above, is particularly useful in the case in which the multiplexer is used in a muscular or neuromuscular electrical stimulator.

For different biomedical applications or for other scopes of use of the multiplexer 1, the output stages $M_I$ may however have different structure and functionality and comprise only the output circuit $NET_1$.

It has been seen in practice how the high voltage switch circuit 1, according to the present invention, allows the set objects to be achieved.

With respect to prior art devices, the switch circuit 1 has improved functionalities, in terms of reduction of dissipated power and high impedance of inputs/outputs.

The switch circuit 1 ensures effective high impedance of inputs and outputs. It is arranged in such a manner that the voltages present between the terminals of the input port IN, of any output port $O_I$ and of the buffer output BF are virtually floating with respect to ground.

An advantage of the switch circuit 1 is the absence of working point bias currents for the active elements (transistors). This substantially reduces the power consumption to what is caused by leakage currents in the transistors.

Additional power consumption in active state is caused by charging/discharging of the parasitic capacitances trough the polarization currents $I_{P1}$, $I_{P2}$. This can be minimized through reducing the time periods during which the control signals $C_1$, $C_2$ are at a logic level commanding the ON state for the switches $T_1$, $T_2$, $T_5$, $T_6$. This is basically a design factor that depends on the parasitic capacitances, mainly in said switches.

The switch circuit 1 is particularly suitable for operating in the presence of high voltages to the terminals of the input port IN or of the output port.

For this purpose, it is sufficient to select in the most appropriate manner the type of transistor of each output stage.

The switch circuit 1 is characterized by considerable flexibility of use.

It is particularly suitable for use in biomedical applications, such as in a muscular or neuromuscular electrical stimulator.

In this application, the use of the output circuits $NET_1$ and $NET_2$ for the output stage $M_I$, according to the description above, enables simple and effective adjustment of the polarity and time distribution of the output current $I_{LI}$, at each output port $O_I$.

However, the switch circuit 1 can be easily integrated in other biomedical applications, for example in ultrasonic devices or micro-electromechanical devices or systems (MEMS).

The switch circuit 1 has a simple structure and is easy and inexpensive to produce at industrial level, with manufacturing techniques using discrete or integrated components.

The invention claimed is:

1. A high voltage switch circuit characterized in that it comprises:
   a constant current generator circuit adapted to provide a predefined constant current;
   an input port, which has a positive terminal and a negative terminal, which are electrically connected to the constant current generator circuit, so that said input port receives the predefined constant input current;
   an output port, which has a positive terminal and a negative terminal;
   a first output having a positive terminal and a negative terminal, which are electrically connected with the terminals of said output port;
   a first switch and a second switch that operate as current switches and are field effect transistors of complementary type, said first switch having a source terminal electrically connected to the positive terminal of said input port to receive the predetermined constant current from the constant current source and a drain terminal electrically connected to the positive terminal of the first output, said second switch having a source terminal electrically connected to the negative terminal of said input port and a drain terminal electrically connected to the negative terminal of said first output;
   a buffer stage that is electrically connected to the positive and negative terminals of said input port and that has a buffer output having a positive terminal and a negative terminal, said buffer stage comprising:
      first and second sensing circuits configured to sense the voltages of the positive and negative terminals of said input port, respectively;
      first and second follower circuits respectively configured to provide voltages at the positive and negative terminals of said buffer output, which follow the voltages sensed by said first and second sensing circuit at the positive and negative terminals of said input port, respectively;
   a first control terminal for providing a first control signal of logic high or logic low directly to a first voltage level translator;
   the first voltage level translator being electrically connected with the terminals of said buffer output, with first and second gate terminals of said first and second switch and with said first control terminal, said first voltage level translator being configured to provide a first and second gate voltage at said first and second gate terminals to control said first and second switch through said first control signal, said first and second switch, controlled by said first control signal, enabling or disabling the flow of the constant input current from said input port to said output port, depending on said first control signal;

wherein said first voltage level translator comprises a third transistor and a fourth transistor to provide said first and second gate voltages, said third and fourth transistor being electrically connected with said first control terminal and to ground, respectively, or vice versa, so as to be controlled by said first control terminal according to the state of said first control signal.

2. The high voltage switch circuit, according to claim 1 characterized in that said first voltage level translator comprises a first over-voltage protection element that is electrically connected with the first gate terminal of said first switch and the positive terminal of said input port and a second over-voltage protection element that is electrically connected with the second gate terminal of said second switch and the negative terminal of said input port.

3. The high voltage switch circuit, according to claim 1, characterized in that said buffer stage comprises:

said first sensing circuit electrically connected with the positive terminal of said input port, with a first sensing node and with a first power supply, said first sensing circuit being configured to sense the voltage of the positive terminal of said input port and establish a voltage offset with respect thereto;

said first voltage follower circuit electrically connected with said first sensing node, with the positive terminal of the buffer output and with a second power supply, said first voltage follower circuit being configured to provide a voltage at the positive terminal of the buffer output, which follows the voltage of the positive terminal of said input port;

said second sensing circuit electrically connected with the negative terminal of said input port, with a second sensing node and with a third power supply, said second sensing circuit being configured to sense the voltage of the negative terminal of said input port and establish a voltage offset with respect thereto;

said second voltage follower circuit electrically connected with said second sensing node, with the negative terminal of said buffer output and with a fourth power supply, said second voltage follower providing a voltage at the negative terminal of the buffer output, which follows the voltage of the negative terminal of said input port.

4. The high voltage switch circuit, according to claim 1, characterized in that it is operatively associated with or it comprises a control stage that outputs said first control signal.

5. The high voltage switch circuit, according to claim 1, characterized in that it comprises:

a second output having a positive terminal and a negative terminal, which are electrically connected with the terminals of said output port;

a fifth switch and a sixth switch that operate as current switches and are field effect transistors of complementary type, said fifth switch having a source terminal electrically connected to the positive terminal of said input port and a drain terminal electrically to the positive terminal of the second output, said sixth switch having a source terminal electrically connected to the negative terminal of said input port and a drain terminal electrically connected to the negative terminal of said second output;

a second control terminal for providing a second control signal;

a second voltage level translator electrically connected with the terminals of said buffer output, with third and fourth gate terminals of said fifth and sixth switch and with said second control terminal, said second voltage level translator being configured to provide a third and fourth gate voltage at said third and fourth gate terminals to control said fifth and sixth switch through said second control signal, said fifth and sixth switch, controlled by said second control signal, enabling or disabling the flow of an input current from said input port to said output port, depending on said second control signal.

6. The high voltage switch circuit, according to claim 5, characterized in that said first output is electrically connected with said output port with a direct polarity and said second output is electrically connected with said output port with an inverse polarity, or vice versa.

7. The high voltage switch circuit, according to claim 5, characterized in that said second voltage level translator comprises a seventh transistor and an eighth transistor to provide said third and fourth gate voltages, said seventh and eighth transistor being electrically connected with said second control terminal and to ground, respectively, or vice versa, so as to be controlled by said second control terminal according to the state of said second control signal.

8. The high voltage switch circuit, according to claim 5, characterized in that said second voltage level translator comprises a third over-voltage protection element that is electrically connected with the third gate terminal of said fifth switch and the positive terminal of said input port and a fourth over-voltage protection element that is electrically connected with the fourth gate terminal of said sixth switch and the negative terminal of said input port (IN).

9. A high voltage current multiplexer characterised in that it comprises a high voltage switch circuit, according to claim 1.

10. A muscular or neuromuscular electrical stimulator characterized in that it comprises a high voltage switch circuit according to claim 1.

11. An ultrasonic device characterized in that it comprises a high voltage switch circuit (1), according to claim 1.

12. A micro-electromechanical device characterized in that it comprises a high voltage switch circuit according to claim 1.

* * * * *